(12) United States Patent
Garabet

(10) Patent No.: US 7,563,258 B2
(45) Date of Patent: *Jul. 21, 2009

(54) METHOD AND APPARATUS FOR PRESSURIZING A BODY CAVITY FOR DIAGNOSTIC AND REHABILITATIVE PURPOSES

(76) Inventor: Anthony Garabet, 840 N. Pennsylvania La., Glendora, CA (US) 91741

(*) Notice: Subject to any disclaimer, the term of this patent is extended or adjusted under 35 U.S.C. 154(b) by 0 days.

This patent is subject to a terminal disclaimer.

(21) Appl. No.: 12/150,187

(22) Filed: Apr. 25, 2008

(65) Prior Publication Data

US 2008/0208168 A1    Aug. 28, 2008

Related U.S. Application Data

(63) Continuation of application No. 11/481,704, filed on Jul. 5, 2006, now Pat. No. 7,364,573, which is a continuation-in-part of application No. 11/000,839, filed on Nov. 30, 2004, now abandoned.

(51) Int. Cl.
*A61M 31/00* (2006.01)

(52) U.S. Cl. .................................................. 604/514

(58) Field of Classification Search ............. 604/65–67, 604/DIG. 13, 43, 39, 97.01, 97.02, 97.03, 604/98.01, 98.02, 99.01–99.04, 100.01–100.03, 604/101.01–101.05, 102.01–102.03, 48, 604/500, 503, 509, 514–520, DIG. 12; 607/113, 607/114, 104, 105; 600/560, 561

See application file for complete search history.

(56) References Cited

U.S. PATENT DOCUMENTS 7,364,573 B2 *   4/2008   Garabet ...................... 604/514

* cited by examiner

*Primary Examiner*—Manuel A Mendez

(57) ABSTRACT

A method and apparatus for both the diagnostic measurement and therapeutic treatment of a body cavity. According to one form of the method of the invention, a fluid (liquid or gas) under pressure is introduced into a selected body cavity while monitoring the pressure or flow of the fluid (liquid or gas) into the cavity. Following pressurization of the body cavity, fluid (liquid or gas) inflow and outflow data is collected and analyzed. The data collected is used to draw various conclusions about the biomechanical properties of the body cavity and the organ in which it is present, and also to draw conclusions about presence or absence of disease as well as the character of disease. According to another method of the invention a fluid (liquid or gas) is controllably infused into the body cavity to controllably expand the body cavity for purposes of therapeutic treatment.

13 Claims, 10 Drawing Sheets

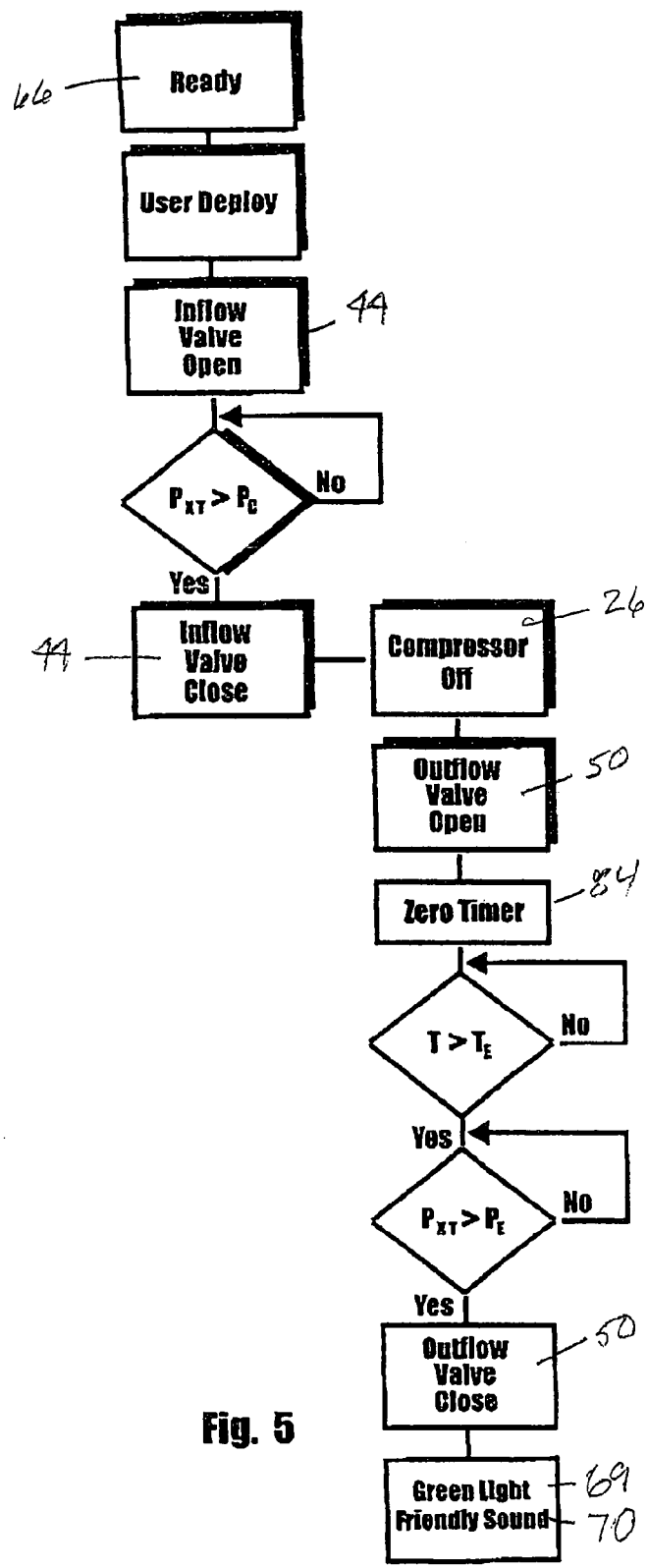
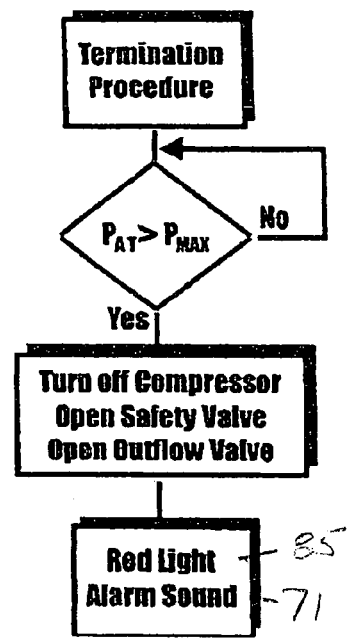
Fig. 5
Fig. 6

|  | inflow rate ml/sec | ref. time sec. | ref. Press mmHg | Trig. Press. mmHg | Maximum Pressure mm Hg | inflow Time sec. | outflow Time sec. | cycle Time sec. | Cumulative inflow time seconds |
|---|---|---|---|---|---|---|---|---|---|
| 1 | 20 | 4.1 | 50 | 50 | 50 | 1.8 | 11.8 | 13.6 | 1.8 |
| 2 | 20 | 4.1 | 50 | 50 | 50 | 6.5 | 16.5 | 23 | 8.3 |
| 3 | 20 | 4.1 | 29 | 39 | 50 | 6.2 | 16.2 | 22.4 | 14.5 |
| 4 | 20 | 4.1 | 29 | 50 | 50 | 0.2 | 10.2 | 10.4 | 14.7 |
| 5 | 20 | 4.1 | 46 | 48 | 50 | 4.4 | 14.4 | 18.8 | 19.1 |
| 6 | 20 | 4.1 | 36 | 43 | 50 | 6 | 16 | 22 | 25.1 |
| 7 | 20 | 4.1 | 30 | 40 | 50 | 5.9 | 15.9 | 21.8 | 31 |
| 8 | 20 | 4.1 | 30 | 40 | 50 | 5.7 | 15.7 | 21.4 | 36.7 |
| 9 | 20 | 4.1 | 30 | 50 | 50 | 0.2 | 10.2 | 10.4 | 36.9 |
| 10 | 20 | 4.1 | 25 | 37 | 50 | 8 | 18 | 26 | 44.9 |
| 11 | 20 | 4.1 | 30 | 40 | 50 | 7 | 17 | 24 | 51.9 |
| 12 | 20 | 4.1 | 25 | 37 | 50 | 5.8 | 15.8 | 21.6 | 57.7 |
| 13 | 20 | 4.1 | 31 | 40 | 50 | 5.8 | 15.8 | 21.6 | 63.5 |
| 14 | 20 | 4.1 | 21 | 35 | 50 | 6.9 | 16.9 | 23.8 | 70.4 |
| 15 | 20 | 4.1 | 21 | 50 | 50 | 0.2 | 10.2 | 10.4 | 70.6 |
| 16 | 20 | 4.1 | 29 | 39 | 50 | 6 | 16 | 22 | 76.6 |
| 17 | 20 | 4.1 | 22 | 36 | 50 | 6.1 | 16.1 | 22.2 | 82.7 |
| 18 | 20 | 4.1 | 21 | 35 | 50 | 9.7 | 19.7 | 29.4 | 92.4 |
| 19 | 20 | 4.1 | 28 | 39 | 50 | 6.7 | 16.7 | 23.4 | 99.1 |
| 20 | 20 | 4.1 | 21 | 35 | 50 | 8 | 18 | 26 | 107.1 |
| 21 | 20 | 4.1 | 22 | 36 | 50 | 9 | 19 | 28 | 116.1 |
| 22 | 20 | 4.1 | 27 | 38 | 50 | 9.9 | 19.9 | 29.8 | 126 |
| 23 | 20 | 4.1 | 27 | 50 | 50 | 1.3 | 11.3 | 12.6 | 127.3 |
| 24 | 20 | 4.1 | 27 | 50 | 50 | 3.3 | 13.3 | 16.6 | 130.6 |
| 25 | 20 | 4.1 | 24 | 37 | 50 | 7.2 | 17.2 | 24.4 | 137.8 |
| 26 | 20 | 4.1 | 29 | 39 | 50 | 9.3 | 19.3 | 28.6 | 147.1 |
| 27 | 20 | 4.1 | 33 | 41 | 50 | 4.5 | 14.5 | 19 | 151.6 |
| 28 | 20 | 4.1 | 38 | 44 | 50 | 4.7 | 14.7 | 19.4 | 156.3 |
| 29 | 20 | 4.1 | 28 | 39 | 50 | 5.1 | 15.1 | 20.2 | 161.4 |
| 30 | 20 | 4.1 | 38 | 44 | 50 | 4.4 | 14.4 | 18.8 | 165.8 |
| 31 | 20 | 4.1 | 39 | 44 | 50 | 4.5 | 14.5 | 19 | 170.3 |
| 32 | 20 | 4.1 | 28 | 39 | 50 | 6.9 | 16.9 | 23.8 | 177.2 |
| 33 | 20 | 4.1 | 28 | 39 | 50 | 9.9 | 19.9 | 29.8 | 187.1 |
| 34 | 20 | 4.1 | 25 | 37 | 50 | 6.6 | 16.6 | 23.2 | 193.7 |
| 35 | 20 | 4.1 | 23 | 36 | 50 | 8.4 | 18.4 | 26.8 | 202.1 |
| 36 | 20 | 4.1 | 23 | 36 | 50 | 9.6 | 19.6 | 29.2 | 211.7 |
| 37 | 20 | 4.1 | 23 | 50 | 50 | 3.6 | 13.6 | 17.2 | 215.3 |
| 38 | 20 | 4.1 | 23 | 50 | 50 | 3.6 | 13.6 | 17.2 | 218.9 |
|  | 20 | 4.1 | 29.2 | 41.6 | 50 | 5.8 | 15.8 | 21.5 |  |

Fig. 10

METHOD AND APPARATUS FOR PRESSURIZING A BODY CAVITY FOR DIAGNOSTIC AND REHABILITATIVE PURPOSES

This is a Continuation Application of application Ser. No. 11/481,704 filed Jul. 5, 2006 now U.S. Pat. No. 7,364,573 which is a Continuation-in-Part of application Ser. No. 11/000,839 filed Nov. 30, 2004 now abandoned.

BACKGROUND OF THE INVENTION

1. Field of the Invention

The present invention relates generally to diagnostic measurements and therapeutic treatment of body cavities. More particularly, one form of the invention concerns a method and apparatus for making dynamic biomechanical measurements of a body cavity. More specifically, the method involves the use of pressure and flow of fluid (liquid or gas) in and out of the body cavity to characterize the elastic properties of the cavity wall and to draw conclusions as to the presence or absence of disease in the organ that contains the cavity. Another form of the invention concerns controlled pressurization of the body cavity for therapeutic purposes, which includes both pain/discomfort resolution and motility rehabilitation.

2. Discussion of the Prior Art

In the past pressurized inflation of body organs and body cavities has been used in a variety of fashions. Some of these uses include air inflation of a body cavity for purposes of visualization (colonoscopy, laparoscopy) and others to deliver vital oxygen into the lungs (artificial ventilation), and intrauterine insufflation to check for patency during an ablative procedure. The use of pressure to extrapolate mechanical properties of tissue or body cavities has also been used to a limited extent in pulmonary function testing.

Other existing technology uses a balloon inserted in the rectum to measure threshold for sensitivity or pain in individuals with Irritable Bowel Syndrome. The machine is called a 'Barostat' (Brouin, M., *Gastroenterology*, 10 Jun. 2000: 122(7): 1771-7). The Barostat can also be used to measure stress/strain relationship of the wall of the rectum (Whitehead, W E, *Dig. Dis. Sci.*, 1 Feb. 1997: 42(2): 223-41; Disrutti, E., *Gastroenterology*, 1 May 1999: 116(5): 1035-42). The current invention measures biomechanical properties without the use of a balloon. The Barostat is not used for therapeutic applications like the current invention.

Biologic tissue is known to be viscoelastic in nature, a property that is known to be altered by disease state.

In Irritable Bowel Syndrome the colon loses its ability to coordinate movement due to increase, decrease, or alteration in its muscular tone. However, as will become apparent from the description which follows, these spastic or flaccid tendencies are measured and treated by the method of the present invention.

SUMMARY OF THE INVENTION

The method and apparatus described in the present invention involves the controlled infusion of a fluid (gas or liquid) into a body cavity both for therapeutic purposes as well as for the purpose of ascertaining the dynamic biomechanical properties of the organ in which the cavity is contained. The methods of the invention are diverse and cover many aspects of medicine. In particular, the diagnostic methods of the invention are concerned with two types of biomechanical measurements, namely measurements during pressurization (load) and during depressurization (unload). Loading occurs when the fluid (liquid or gas) is actively infused into the body cavity, and unloading occurs when the fluid (liquid or gas) is passively allowed to be expelled from the cavity by the organ's own biomechanical rebound.

In one form of the method of the invention a flexible tube is used to connect the body cavity to the apparatus of the invention and this novel method includes the following features:

(a) a pressurizing system capable of producing fluid (liquid or gas) which is calibrated in a manner that is to accurately measure pressure and/or flow during the load phase;

(b) a system that is capable of controllably delivering the fluid (liquid or gas) in a safe manner;

(c) a system that includes tubing that permits the efficient delivery and infusion of the fluid (liquid or gas) into the body cavity;

(d) a system that includes means for accurately monitoring pressure and/or flow characteristics during the inflow or load phase;

(e) a system that includes tubing that enables the fluid (liquid or gas) to be expelled from the body cavity and delivered into a discharge bag;

(f) a system that enables monitoring of pressure and/or flow during the outflow or unload phase;

(g) a system that enables data collection for purposes of interpretation during both the inflow and outflow phases; and (h) a system that provides interactive features which permit the user to adjust the parameters of pressure and/or flow based on the nature of the body cavity being investigated, including:

choosing the initiation pressure during the inflow phase;

choosing the pressure level at which the loading phase ends and the unloading phase begins; that is, during the inflow/outflow transition;

choosing the pressure level at which the unloading phase is terminated;

choosing the maximum pressure allowable within the body cavity during the pressurizing phase;

choosing the maximum volume allowable for infusion in the body cavity; and a system which allows for automatic cessation of pressurization, along with the opening of a safety valve if the pre-set maximum pressure is exceeded.

Once the user of the apparatus initiates a specific study, the study will proceed from inflow to outflow without interruption so long as the pressure within the body cavity remains within predetermined levels. In this regard, the system is designed to permit the user to reset the system and repeat the study under the same or different parameters.

In one form of the diagnostic method of the invention, the apparatus allows for data collection and storage capabilities so that the pressure and flow data can later be used for purposes of interpretation as to the dynamic loading/unloading biomechanical properties of the cavity under investigation. Ultimately, the same data can also be used for therapeutic planning.

The therapeutic features of the invention allow for the following:

a system to pressurize a cavity (colon) in a certain therapeutic fashion to reduce pain or abnormal perceptions/sensations.

a system to allow the tissue (musculature of the colon) to exert effort to expel fluid (liquid or gas) in a certain controlled, predetermined fashion.

a system to tailor the inflation/deflation parameters based on the disease process of the organ in question.

a system to manipulate the parameters of therapeutic inflation/deflation based on biomechanical feedback system and on the pain/discomfort reduction effectiveness, or other subjective perceptions of relief expressed by the patient.

The apparatus of the invention can also be used for motility rehabilitative purposes. More particularly, the apparatus can be used to train body cavities with motility dysfunction to function more normally. This can be achieved with repetitive inflation and deflation of the body cavity. With repeated training of the body cavity using the device, the organ can be rehabilitated in a manner to achieve long-term, sustainable normal functional motility.

When used for rehabilitation purposes the apparatus:
(a) can be used to pressurize a selected body cavity in a repetitive fashion as predetermined by the user;
(b) can be used to determine the strengths and weaknesses of the body cavity, hence allowing the user to design a treatment plan;
(c) can be used to carry out procedures that are customized for the unique biomechanical features of a body cavity;
(d) can be used to restrain and restrict or even stimulate the mechanical response of a body cavity to a finite and predetermined range;
(e) can be used to cause the body cavity to be rehabilitated and "rewired" neurologically for proper motility and biomechanical functioning; and
(f) can be customized for each individual patient using modes and settings of the system. These variables include: flow rate, pressure, pressure rate change, interval between cycles, amplitude of cycle, variations between cycles, resistance of outflow, and number of cycles. Variations can also be made within same treatment mode (intratreatment variation), variation from one treatment to the next (intertreatment variations) and interactive variations (programmed).

BRIEF DESCRIPTION OF THE DRAWINGS

FIG. 5 is a generally diagrammatic view further illustrating the sequence of operation of one form of the apparatus of the invention.

FIG. 6 is a generally diagrammatic view illustrating the automatic termination feature of the invention.

FIG. 10 is a tabulation of pressure measurements collected in the conduct of one form of the method of the invention.

DESCRIPTION OF THE INVENTION

Figure 1:
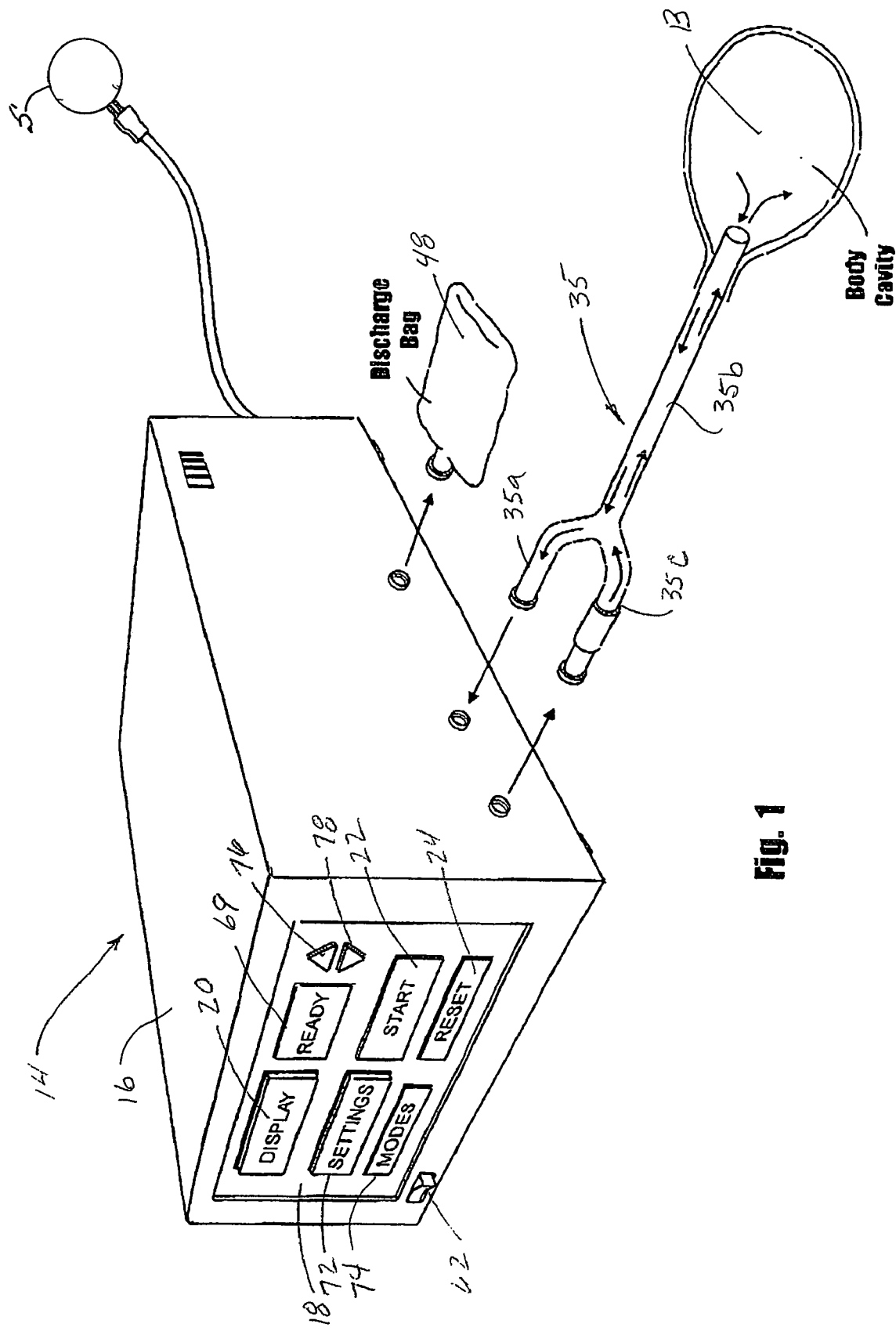
FIG. 1 is a generally perspective view of one form of the apparatus of the invention for making biomechanical measurements of a body cavity.
Figure 2:
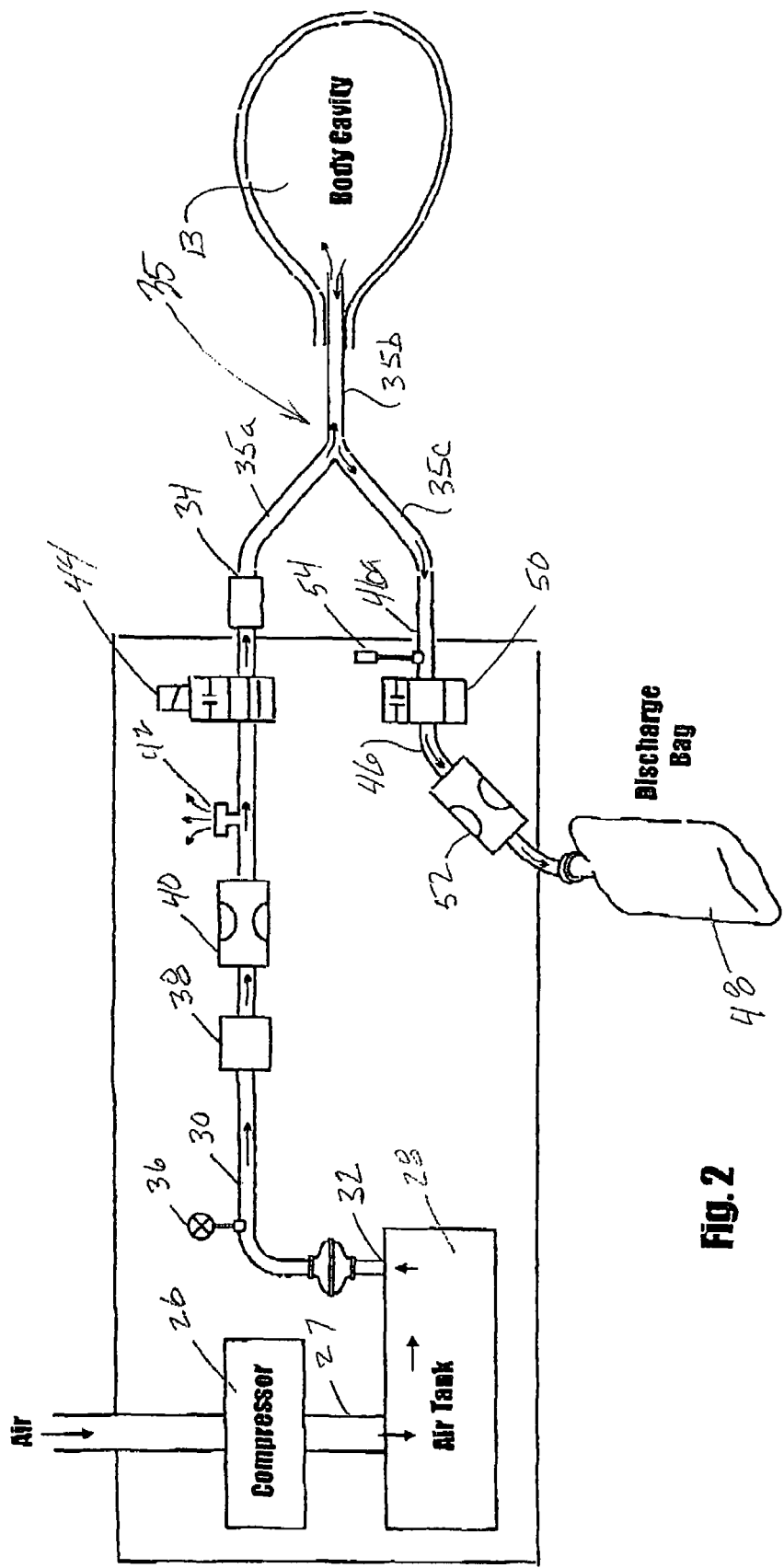
FIG. 2 is a generally diagrammatic view illustrating the various components that make up apparatus of the invention shown in FIG. 1.

Referring to the drawings and particularly to FIGS. 1 and 2, one form of the apparatus of the invention is there shown and generally designated by the numeral 14. The apparatus here comprises a hollow housing 16 having a front panel 18 upon which a display button 20 is mounted. Front panel 18 also carries a start button 22 and a reset button 24. Disposed within the hollow housing 16—See FIG. 2—is a conventional air compressor 26 which draws air from atmosphere, compresses it and introduces the compressed air into an air tank 28 via a conduit 27.

Interconnected with air tank 28 is an elongated fluid (liquid or gas) flow conduit that comprises a first segment 30 that has a proximal end 32 and a distal end 34. Proximal end 32 is connected to air tank 28 while distal end 34 communicates with the first portion, or inflow branch 35a of an interface means, shown here as a disposable external tubing assembly 35. The second portion, or main trunk 35b of tubular assembly 35 communicates with the body cavity "B" that is to be pressurized. Disposed intermediate proximal end 32 and distal end 34 of the first segment 30 of the fluid (liquid or gas) flow conduit is a pressure gauge 36, a pressure regulator 38, a flow regulator 40 and a safety valve 42. Pressure gauge 36 is used to verify that there is sufficient pressure in conduit segment 30 to initiate the inflow cycle of one form of the method of the invention. The pressure regulator 38 ensures uniformity of pressure during the conduct of the method of the invention and the flow regulator 40 ensures uniformity of air flow through the segment 30. The safety valve 42, which communicates with atmosphere, remains closed during the operational sequences of the method unless the pressure in the system exceeds a predetermined maximum level in which case the safety valve automatically opens to vent the system to atmosphere. Also disposed intermediate the proximal and distal ends of segment 30 is an inflow valve 44 that remains in a closed position while the apparatus is in a standby mode.

As illustrated in FIG. 2 of the drawings, the third portion, or outflow branch 35c of the external tubing assembly 35 communicates with a second segment 46 of the fluid (liquid or gas) flow conduit. This second segment has a proximal end 46a and a distal end 46b that is interconnected with a disposable discharge bag 48. Disposed between the proximal and distal ends of second segment 46 are an outflow valve 50 and an outflow regulator 52 for regulating fluid (liquid or gas) flow through segment 46. Communicating with second segment 46, proximate its proximal end 46a, is the important sensor means of the invention shown here as a pressure sensor 54. Pressure sensor 54 senses the pressure within second segment 46, generates an appropriate pressure signal and transmits the pressure signal to the control means, or microprocessor, of the invention which is housed within housing 16.

Figure 3:
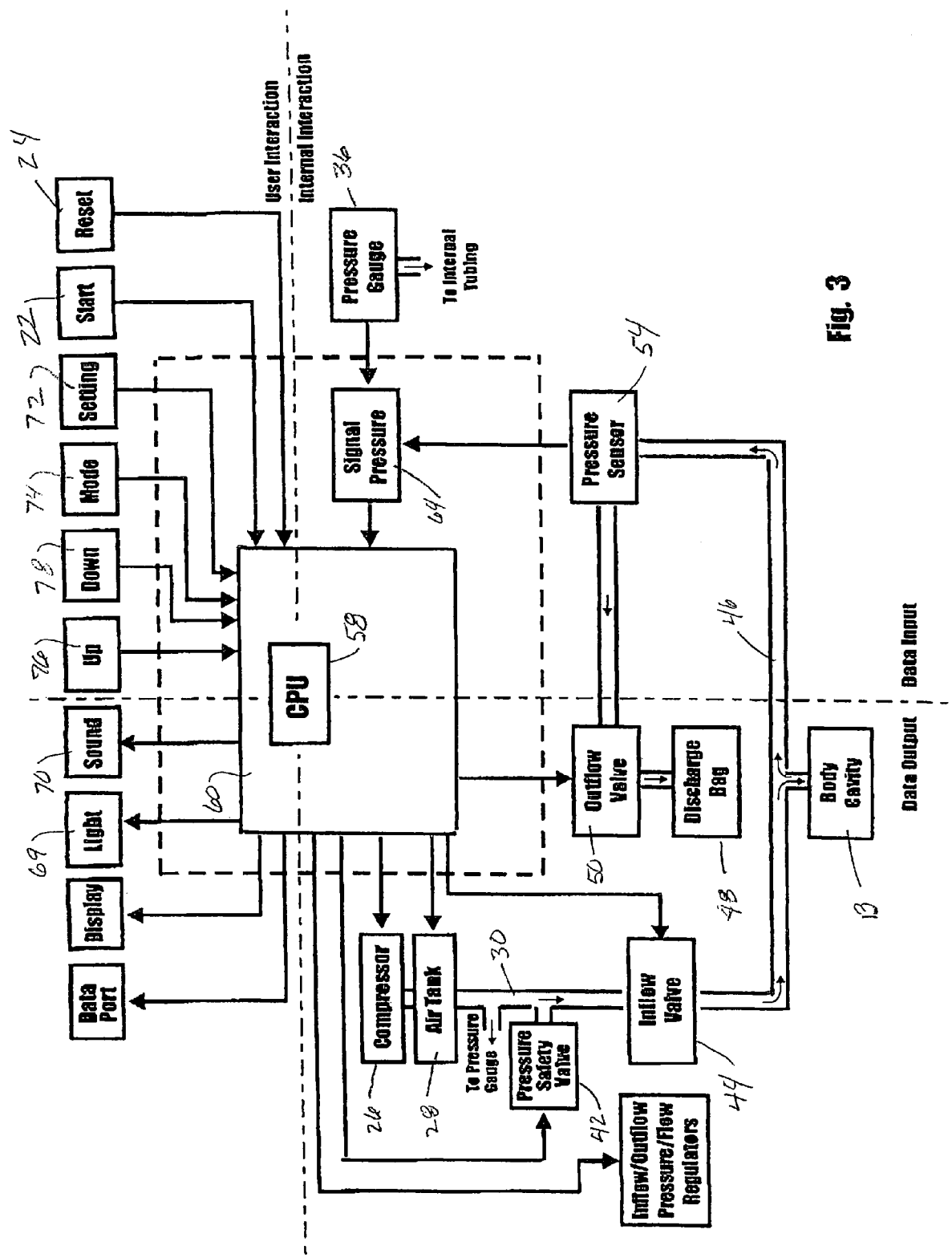
FIG. 3 is a generally diagrammatic view illustrating the operational interrelationship among the various components of one form of the apparatus of the invention.

Turning also to FIG. 3 of the drawings, it can be seen that the control means of the present form of the invention comprises the central processing unit, CPU, 58 of a conventional microprocessor 60 that is interconnected with, and controls the operation of, many of the operating components that make up the apparatus of the invention.

In the conduct of one form of the method of the invention, the user first activates the apparatus by manipulating the main switch 62 (FIG. 1). Upon activation of the device, the control means, or CPU 58, which has been appropriately programmed in a manner well known to those skilled in the art, will cause the inflow valve 44 to open and will energize the compressor 26 so as to cause—See FIGS. 2 and 3—the controlled pressurization of air tank 28 and the segment 30. When the pressure in segment 30 reaches a predetermined level as determined by the pressure gauge 36, the CPU will receive an appropriate signal from the pressure gauge 36 via the signal pressure indicator 64. At this point, the CPU will cause the illumination of an illuminable green, ready light 69, which is mounted on panel 18 of housing 16, and will also cause an audio signal to be emitted by the audio signaling device 70 (FIG. 3) carried by housing 16. Upon receiving these signals the user will set the appropriate operating parameters of the method that is to be conducted. In the present form of the invention this is accomplished through use of the setting 72, the mode 74, the up 76 and the down 78 features of the apparatus (FIG. 3). After the appropriate operating parameters have been set, the user pushes the start button 22 causing the CPU to commence the testing cycle by first opening the inflow valve 44 thereby permitting the controlled pressurization of the body cavity "B". In accordance with this method of the invention, the pressurization of the body cavity will be constantly monitored by the sensor means or pressure sensor 54. When the pressure reaches a pre-set level, the CPU will cause the inflow valve 44 to close, the compressor to be de-energized and the outflow valve 50 to open. Opening of the outflow valve 50 signals the commencement of the outflow, or unload, phase of the method of the invention.

At the commencement of this important outflow phase, the body cavity "B" will recoil in a manner to exert a rebound pressure that will drive the air from the body cavity through conduit 46 and into the disposable collection bag 48 via the flow regulator 52. The end of the outflow cycle occurs when the pressure within the system drops below a predetermined level. At this time the outflow valve 50 will be automatically closed by the CPU. It is to be understood that, if during the testing process, the pressure within segment 30 exceeds a predetermined level as determined by the pressure gauge 36 and the sensor 54, the CPU will automatically de-energize the compressor 26 and will cause the safety valve 42 to automatically open.

If the user wishes to repeat the test, the reset button 24 (FIG. 1) is pushed. This will cause the opening of the outflow valve 50 for a predetermined, short period of time in order to decompress the external tubing assembly 35 and the body cavity space "B". The CPU will then close the outflow valve 50 and close the inflow valve 44 (FIG. 3) and will energize the compressor 26. As before, when the pressure within segment 30 reaches a predetermined level the green ready light will be illuminated and the testing method can be repeated in the manner previously described.

Figure 4:
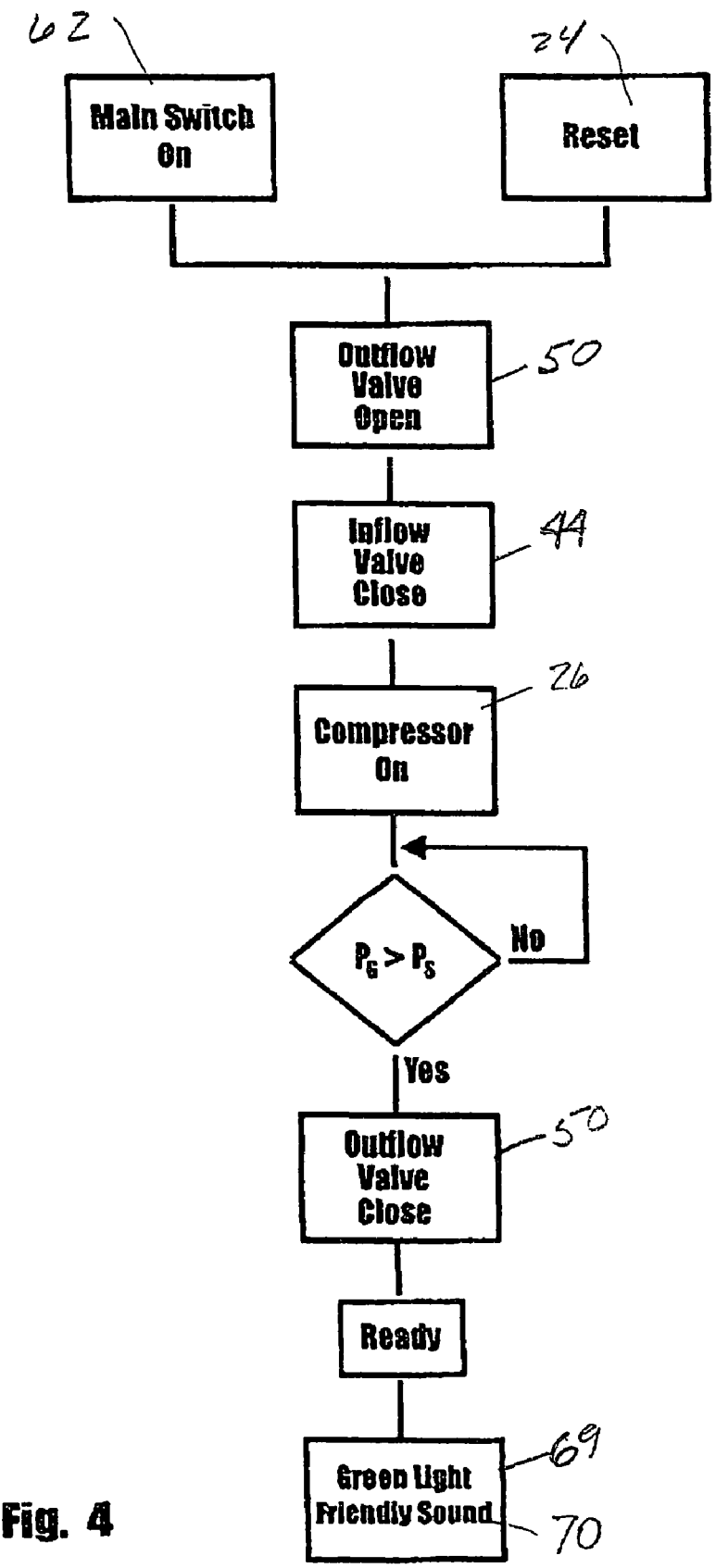
FIG. 4 is a generally diagrammatic view illustrating the sequence of operation of one form of the priming method of the invention.

Turning next to FIG. 4 of the drawings, the priming method of the invention is there illustrated. This priming step can be accomplished in one of two ways, either by pressing the reset button 24 or by operating the main switch 62 (FIG. 1). In either case, this causes outflow valve 50 to open, the inflow valve 44 to close and the compressor 26 to be energized. The pressure within segment 30 is then determined using pressure gauge 36, and this pressure is compared with the pre-set starting threshold pressure. This step is repeated until the pressure within the segment 30 exceeds the desired starting threshold pressure at which point the microprocessor closes the outflow valve 50, causes the green light 69 to illuminate and causes an audio signal to be generated 70.

Referring next to FIG. 5 of the drawings, the method of the present invention is further illustrated there. Following appropriate programming of the microprocessor unit of the invention and after the apparatus has been interconnected with a source of electrical power "S" (FIG. 1), the ready button 66 is pressed to start the testing procedure. As indicated in FIG. 5, this causes the inflow valve 44 to open. At this point the pressure sensor 34 monitors the pressure $P_{XT}$ in the external tubing assembly 35 and compares this pressure to a pre-set critical pressure. At such time that the pressure $P_{XT}$ exceeds the predetermined critical pressure $P_C$, the CPU closes the inflow valve 44, de-energizes the compressor 26 and opens the outflow valve 50. At this time the apparatus, or Zero, timer 84, which is set at zero, is started. Once the timer reaches a predetermined elapsed time as, for example, 10 seconds, the $P_{XT}$ is monitored using sensor means until it reaches a level less than a predetermined ending pressure $P_E$. When this pressure is reached, the cycle is finished, the green light 69 is energized and an audio signal is generated 70.

Turning to FIG. 6 of the drawings, the automatic termination feature of the method of the invention is there illustrated. This feature of the invention, which is preprogrammed in the microprocessor, is triggered when the pressure $P_{AT}$ in the conduit 30, as measured by gauge 36 or sensor 54, exceeds a predetermined pressure $P_{MAX}$. When this happens, the safety valve is opened, the compressor 26 is automatically de-energized, the outflow valve 50 is automatically opened, a red signal light 85 is illuminated and an audio alarm is sounded 71.

Figure 7:
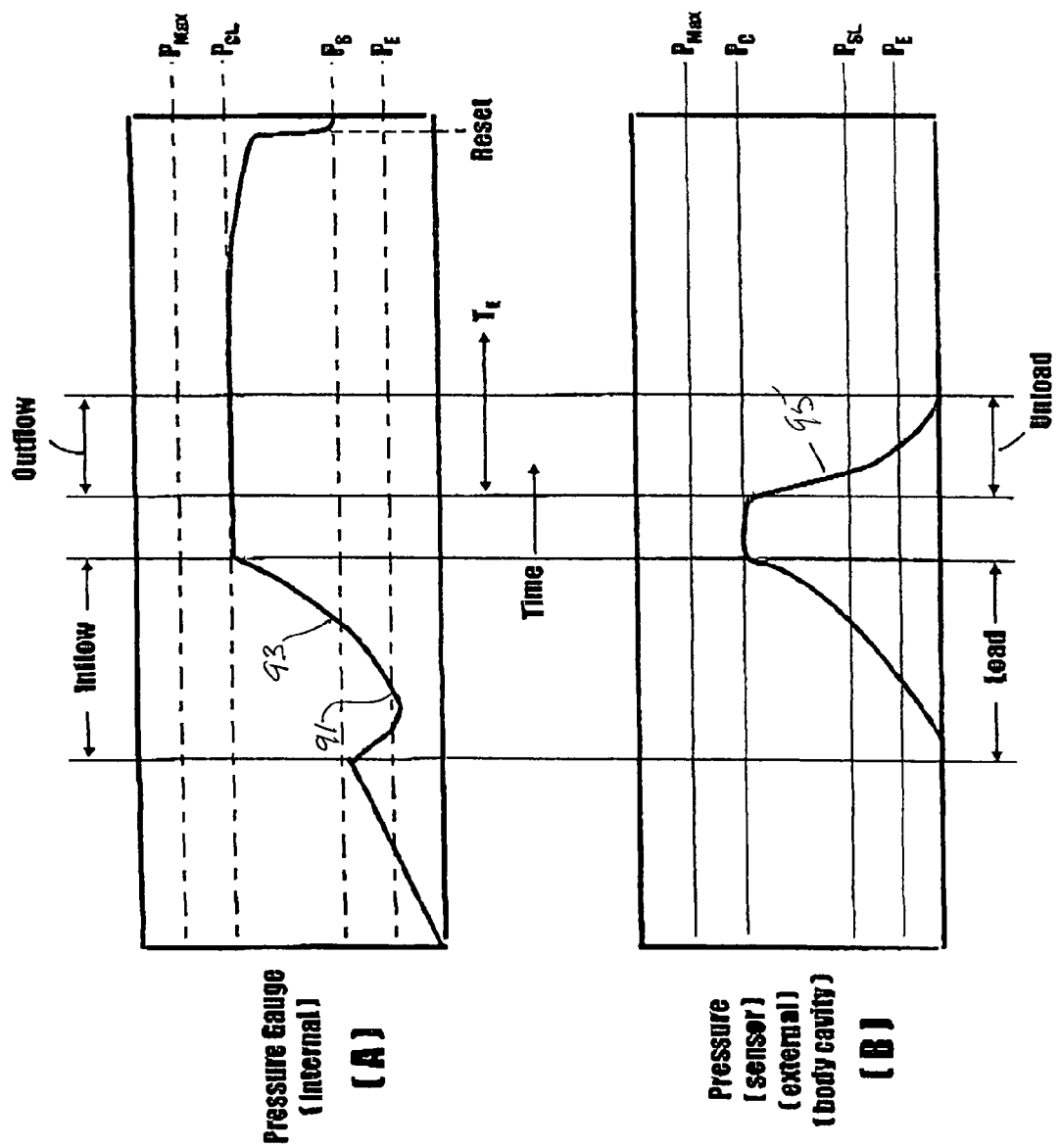
FIG. 7 is a graphical representation illustrating operational pressures as a function of time during the performance of an alternate, diagnostic form of the method of the invention.

FIGS. 7A and 7B graphically depict pressure changes in the system as a function of time during the conduct of the diagnostic method of the invention. More particularly, FIG. 7A depicts pressure changes in segment 30 of the internal system as measured by pressure gauge 36. Similarly, FIG. 7B depicts pressure changes in the external system, or disposable assembly 35 during the loading and unloading cycles of the diagnostic method of the invention. As illustrated in FIG. 7A, as the air is introduced into the body cavity "B" at the starting pressure $P_S$, which exceeds the external pressure $P_E$, the pressure first decreases and then progressively increases as a function of time. As shown by segment 91 of FIG. 7A, the initial pressure change is relatively slow. However, as the body cavity exerts resistance to the inward flow of air, the pressure increases more rapidly as illustrated by segment 93 of FIG. 7A. When the pressure reaches a critical level $P_C$, the pressure curve flattens indicating the completion of the inflow study. The various diagnostic parameters that can be extracted from the graphical representation include but are not limited to the initial slope as depicted by segment 91, the maximum slope (93), the time to reach maximum slope, etc. Analysis of these parameters, which reveal the elastic properties of the body cavity, can be used to draw conclusions as to the presence or absence of disease in the organ that contains the cavity.

Referring to FIG. 7B, once the peak pressure $P_C$ is reached the compressor is de-energized by the CPU and the outflow valve 50 is opened. This permits the air under pressure to flow from the body cavity "B" toward the discharge bag 48. As indicated by the curved segment 95 there is initially a steep decline in pressure followed by a slower decline in pressure. The parameters that can be extracted from the graphical representation include the initial slope of the curve, the peak slope $P_{SI}$ of the curve and the time to reach a 50% decline in pressure. These parameters can also be used to draw conclusions as to the condition of the organ that contains the cavity.

It is to be understood that many different types of loading and unloading studies can be performed using the apparatus of the invention to extract a variety of biomechanical parameters and functional motility characteristics of the organ under study. Furthermore, it is to be appreciated that, while the figure drawings illustrate studies of pressure as a function of time, studies can also be undertaken involving data collection and plotting of fluid (liquid or gas) flow as a function of time, rather than pressure change as a function of time, along with other fluid (liquid or gas) mechanics correlations.

Figure 8:
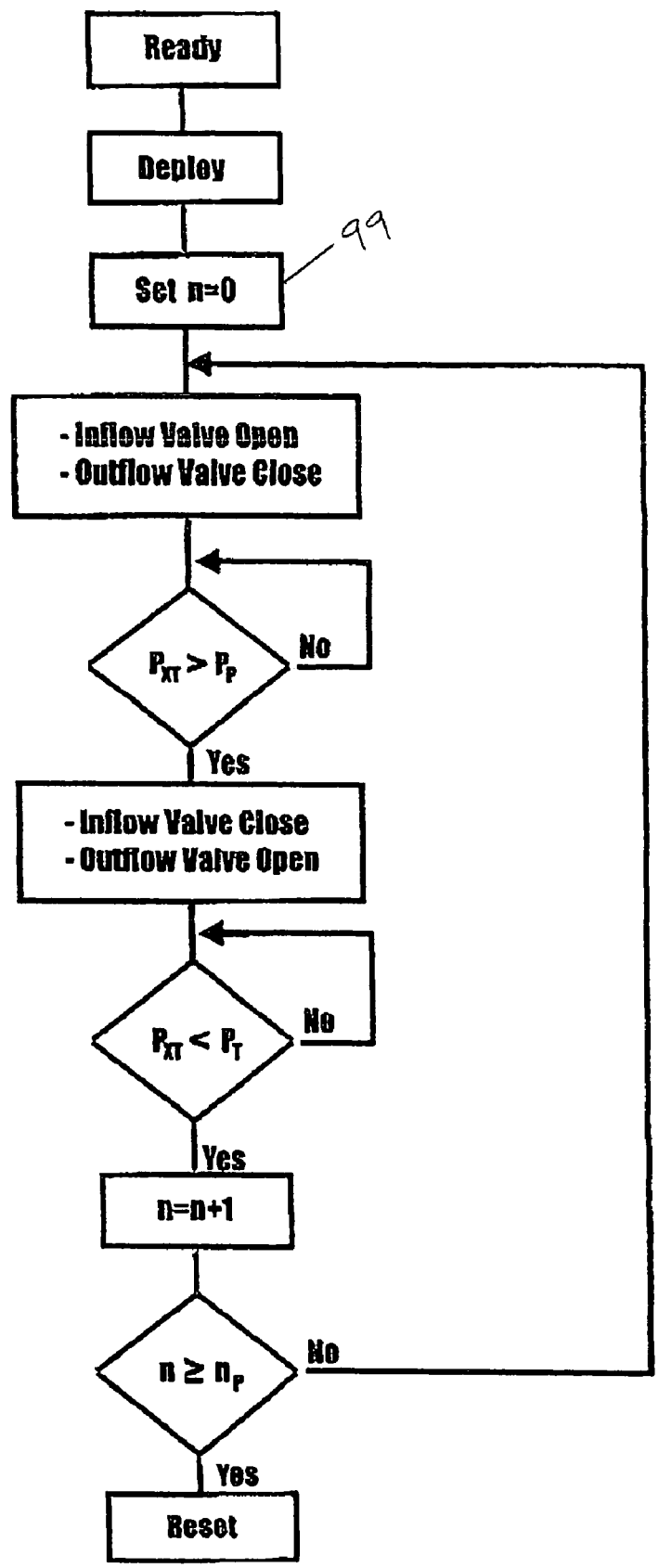
FIG. 8 is a generally diagrammatic view further illustrating the sequence of operation of an alternative rehabilitation form of the apparatus of the invention.
Figure 9:
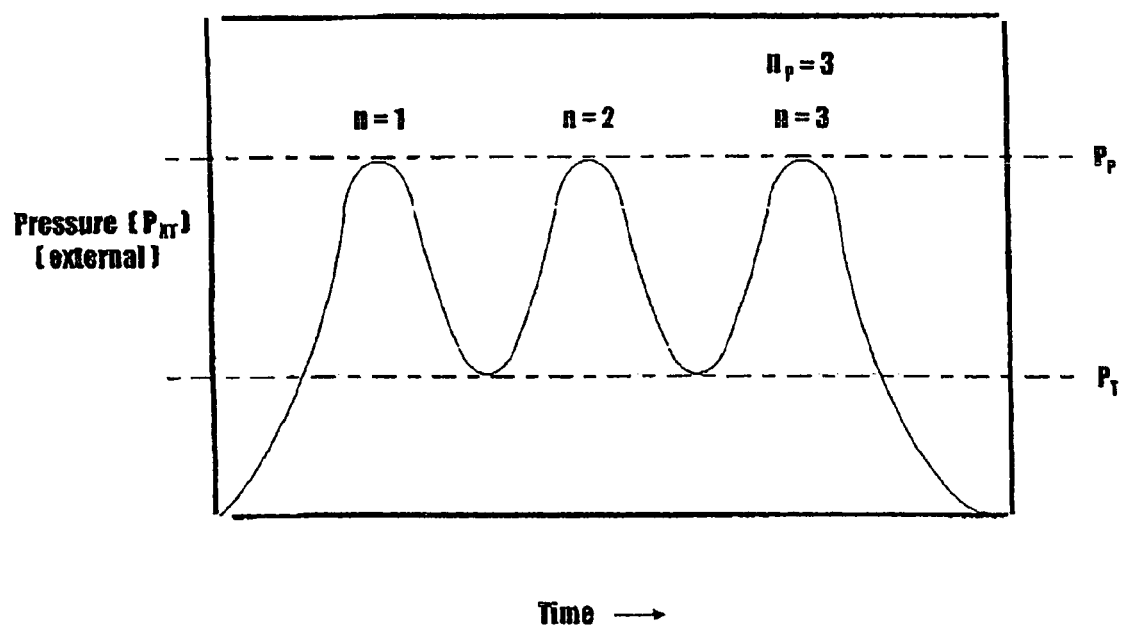
FIG. 9 is a graphical representation illustrating pressure as a function of time during the rehabilitation method of the invention.

Turning to FIGS. 8 and 9 of the drawings, the various steps in an alternate form of the method of the invention for purposes of rehabilitation are there illustrated. More particularly, as previously mentioned, the apparatus can be used to train body cavities with motility dysfunction to function more normally. By way of example, this can be achieved by repeatedly inflating and deflating the body cavity. This technique can also be used to determine the strengths and weaknesses of a particular body cavity and can be customized for each individual patient. As indicated in FIG. 8, when the apparatus is in the "ready" status, the "modes" and "settings" buttons (74, 72 of FIG. 1) can be used to place the apparatus in the rehabilitation mode at the appropriate setting. When this is done the cycle counter 99 sets itself to n=0. The first cycle then begins with the microprocessor opening the inflow valve 44 and closing the outflow valve 50. This will permit controlled pressurization of the body cavity. The pressurization of the body cavity is monitored by the sensor 54 and appropriate pressure signals are transmitted to the CPU. The CPU compares the pressure $P_{XT}$ in the external tubing system 35 with a predetermined peak pressure $P_P$ (FIG. 9). At such time as the external pressure exceeds the peak pressure, the CPU automatically closes the inflow valve 44 and opens the outflow valve 50. This permits fluid (liquid or gas) outflow from the body cavity in a manner to cause a decrease in the pressure. When the pressure decreases below a predetermined pressure $P_T$, the counter 99 records the completed cycle as n=n+1. If the number of cycles is below the planned number of cycles $n_P$, i.e., $n<n_P$, another cycle is automatically commenced. If the number of cycles reaches or exceeds the planned number of cycles, the system will automatically go into the reset mode (FIG. 8).

It is to be understood that the methods of the invention for rehabilitation can be customized for a particular patient with the pressure levels, the number of cycles to be undertaken and a variety of modes and settings specially selected for that particular patient. The settings are extracted from data obtained during the diagnostic phase of the invention when used on that patient undergoing the therapeutic intervention.

Figure 11:
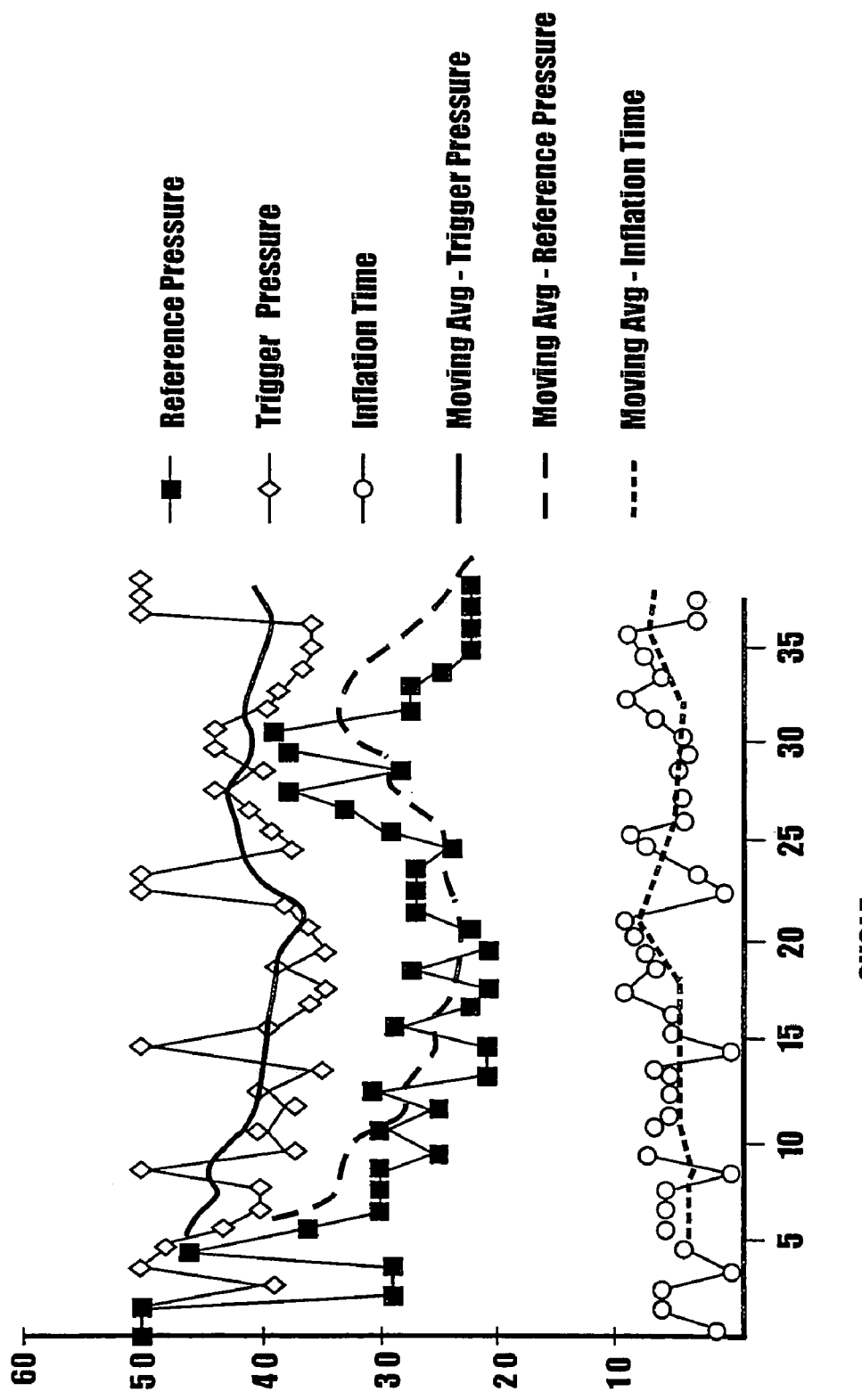
FIG. 11 is a graphical representation of pressure measurements collected in the conduct of one form of the method of the invention.

Referring next to FIGS. 10 and 11, these Figures exhibit exemplary data taken from clinical tests carried out in accordance with one form of the method of the present invention, namely the controlled inflation and deflation of the colon of the patient.

The following terms, which appear in FIG. 10 and which are used in the discussion and claims which follow, have the following meanings:

Number of cycles: The total number of cycles delivered to one patient in the course of one treatment.

Duration of cycle: The length of time of each cycle which is calculated by adding the inflation and deflation time.

Inflow time: The Length of time during which air is inflated in the colon in any given cycle.

Outflow time: The Length of time during which air is allowed to escape out of the colon in any given cycle.

Maximum Time: The time cap imposed on the inflow phase of each cycle. If the inflation duration reaches the "Maximum Time", the device will automatically shut-off the pump and switch to deflation.

Duration of a full treatment: Duration of a full treatment that is given to any particular patient in one setting. It is equal to the sum of the durations of every cycle within that treatment session.

Maximum Pressure: The maximum pressure allowed to be reached within the colon during any particular treatment. The peak pressure is the back-up trigger that stops the inflation to keep the pressure from rising above safe and tolerable levels.

The first "N" cycles: The first few cycles in the treatment where the inflow is allowed to build up the pressure until the "Maximum Pressure" is reached.

Reference time: The average of the time it takes to reach the "Maximum Pressure" in the first N cycles. If the "Maximum Pressure" is not reached in any given cycle, the reference for that cycle would be the "Maximum Time".

Reference pressure (measured): The pressure measured by the device at the "Reference Time" in any particular cycle subsequent to the $N^{th}$ cycle. It is used as a measure of compliance of the tissue, and also to recalculate the new and adjusted trigger pressure for every cycle. The adjusted trigger pressure is usually lower than the 'peak pressure', hence the term low pressure insufflation.

Trigger pressure (calculated): The pressure that is recalculated during the inflow phase of each cycle based on the tissue compliance or resistance (as deduced from the reference pressure). If the tissue is soft, the reference pressure would be low and the trigger pressure will therefore be lower. If the tissue is firm the trigger pressure will be higher, but never higher than the peak pressure.

Accordingly, the trigger pressure is customized for any given cycle subsequent to the $N^{th}$ cycle, during the inflow phase and is considered a very essential element of this invention. It determines the manner in which the device responds to the tissue.

The inflation rate: The rate at which the pump is set to deliver air or fluid in volume per seconds.

Rest time: The period of time that follows the outflow phase to allow the body cavity to effectively evacuate the fluid.

Total inflow time: The sum of all the inflow times of every cycle within a treatment session. This number can be adjusted and customized by the operator based on the size of the particular body cavity, the weight of the patient, and other physiologic variables In carrying out this latest form of the method of the invention, as the colon is pressurized at a predetermined rate it will controllably expand. One of the critical elements of the method is to insure that the pressurization will stop whenever the pressure reaches a pre-set "Maximum Pressure". The "Maximum Pressure", as defined in the preceding paragraph, is designed to protect the body cavity from injury that can be caused by high pressure. This maximum pressure can range from between about 15 mm Hg and about 100 mm Hg.

Another critical aspect of this latest method of the invention is for the device to record and store the time it takes for the pressure in the body cavity to reach the "Maximum Pressure" in the first N cycles. The average period of time it takes to reach the "Maximum Pressure" in the first N cycles is the "Reference Time". The "Reference Time", as defined in the preceding paragraph can also be an arbitrary fixed number. N could be either a pre-designated number or possibly adjusted by the device in the early stages of the treatment to ensure the collection of reliable time and pressure data. The "Reference Time" is stored and used by the device to adjust parameters in each cycle subsequent to the $N^{th}$ cycle and can range from between about 1 and about 30 seconds.

The "Reference Time" is used in subsequent cycles as follows: After the $N^{th}$ cycle, the device measures the pressure as the time reaches "Reference Time". This Pressure is designated "Reference Pressure" for that particular cycle. This reference pressure is an indication of how compliant the tissue of the body cavity is. As illustrated in FIG. 11, during the particular example there graphed, the reference pressure varied from between about 20 mm Hg and about 40 mm Hg. However, in practice, this pressure can vary from between about 5 mm Hg and about 100 mm Hg. The device automatically averages the "Reference Pressure" and the "Maximum Pressure" in the early stages of each cycle. This average is called the "Trigger Pressure". Whereas the pressure that triggers the stop in pressurtion in the first N cycles is the "Maximum Pressure", the trigger pressure for each cycle subsequent to the $N^{th}$ cycle is about halfway between the "Reference Pressure" and the "Maximum Pressure" (the average). This pressure is dubbed the "Trigger Pressure". As illustrated in FIG. 11, in the example there illustrated, the "Trigger Pressure" ranged from between about 35 mm Hg and about 50 mm Hg. However, in practice, this "Trigger Pressure" can range from between about 5 mm Hg and about 100 mm Hg. Since the Reference Pressure varies from cycle to cycle depending on the compliance of the body cavity, the "Trigger Pressure" will also vary. As a consequence, and in a manner that is critical for the current method, the trigger pressure for subsequent cycles will be lower than the "Maximum Pressure".

It is expected in this latest method of the invention that the colon will become more compliant in the later cycles than the early cycles. This is in response to the pressurization and rehabilitation as well as to the increase in the average radius of the colon in response to residual fluid from earlier cycles. This increase in compliance will cause the tissue resistance to be lower, hence the "Reference Pressure" (Pressure at the "Reference Time") will be lower, and therefore the "Trigger Pressure" will also be lower. Accordingly, the shut-off Trigger for later cycles will be lower than that in the early cycles. The decline in the "Trigger Pressure" in response to increase in body cavity compliance (decreased resistance) is accomplished through the calculations as previously discussed.

More specifically, the "Trigger Pressure" for subsequent cycles is nominally an average of the "Maximum Pressure" and the "Reference Pressure", and, since the "Reference Pressure" is lower than the "Maximum Pressure", the average of the two pressures, the "Trigger Pressure" will be lower than the "Maximum Pressure".

It is an important aspect of the method of the invention that pressurization ceases at lower and lower "Trigger Pressures" as the body cavity becomes more and more compliant. As in prior art, in the absence of such a feature, the device would continue to pressurize up to the same high pressure limit ("Maximum Pressure") in an ever more and more compliant and expanding body cavity. Consequently, unlike the present invention, it will deliver higher amounts of fluid for longer periods of time, filling up the ever more compliant and expanding cavity. In addition to having longer cycles, the number of cycles would be minimal. This is due to the fact that the colon does not have the volume capacity for too many long cycles without the benefit of frequent deflations as called for in the present invention. Few long cycles defeat one of the main objectives of the invention to have numerous and repetitive 'inflation/deflation' short cycles. In fact, in the existing prior art the objective is to completely inflate the body cavity in as little time as possible. By design in the prior art, the "Trigger Pressure" is maintained at the "Maximum Pressure" for the entire length of the procedure to keep the cavity as inflated as possible for adequate visualization. As a result, the physician is able to inflate the entire body cavity with fluid in just a handful of cycles. In this prior art the body cavity is subjected to the same high "Maximum" trigger pressure throughout the procedure without the benefit of deflation and without consideration to the change in tissue biomechanical properties. In this prior art the body cavity is not deflated until after the conclusion of the procedure.

Importantly, long cycles with limited deflation, as seen in the prior art, will likely cause the introduction of fluid volume beyond that which the body cavity can handle and can cause significant discomfort that would cause interruption of the treatment.

An important feature of the method of the present invention is that is not intended for full body cavity inflation and is specifically designed for use in an outpatient setting with no anesthesia but with continuous observation. It is, therefore, critical to deliver a small volume of fluid per cycle followed by adequate deflation to allow the patient to easily tolerate the treatment with a minimum chance of injury.

The period of time during which pressurization continues prior to being 'triggered'-off, is called the "Inflow Time", or pressurization time. This time is, in essence, the duration of inflation, and may vary since the "Trigger Pressure" vanes with each cycle. The "Inflow Time" is a dependent variable that is measured by the device as the period of time between the commencement of pressurization and the "tiggering-off" of pressurization in a given cycle. By way of example, as illustrated in FIG. 11, the inflow time ranged from 1-10 seconds. In practice, the pressurization time can vary from between about 1 and 100 seconds and preferably varies from between about 1 and 50 seconds.

An important aspect of the invention is the cap on the "Inflow Time" of each cycle to a pre-designated level called the "Maximum Inflow Time". As the colon becomes more and more compliant it may exert limited resistance to the inflow of fluid; hence the "Trigger Pressure" calculated for that cycle may not be a low enough trigger and may not be reached. In this situation the inflow cycle will be interrupted due to the expiration of the "Maximum Inflow Time". The limitation imposed by the "Maximum Inflow Time" has the benefit of capping the volume of fluid delivered per cycle into the body cavity. Under such circumstances the inflation phase is terminated due to a time trigger ("Maximum Inflow Time") and not to a pressure trigger ("Trigger Pressure").

Another important aspect of the invention is to allow sufficient time for the fluid that was introduced into the body cavity to be evacuated therefrom as completely as possible. The "Outflow Time", or depressurizing time, is the time provided for the body cavity to evacuate the fluid pumped into the cavity during the inflow phase of the current cycle. The "Outflow Time" is set to be equal to the "Inflow Time" of the current cycle plus a "rest period". If the volume of fluid introduced into the colon is excessive, it may not be completely expelled from the cavity due to inherent limitation on the ability of the body to expel fluid. Failure of the body cavity to completely expel the fluid might lead to accumulation of fluid within it causing the treatment session to be prematurely interrupted due to pain and discomfort. This is true irrespective of the duration of the depressurizing time. In the present invention the "Outflow Time" is longer than the "Inflow Time". It is important that the duration of the "Inflow Time" and "Outflow Time", as well as coordination between the two, is established to allow for effective evacuation that is as comfortable and as complete as possible. An effective evacuation in any particular cycle is critical for the body cavity to be prepared for the subsequent cycle. This will also allow for maximization of the number of inflow/outflow cycles per treatment session. In practice, the "Outflow Time" can range from between about 3 and 300 seconds, but normally varies from between about 5 seconds and about 60 seconds.

Another important aspect of the invention is the cyclical nature of the delivery of fluid to the body cavity to ensure that each cycle is appropriately limited in time and pressure. In practice, the cycle time can range from between about 4 and about 500 seconds with, by way of example, the first cycle time being between about 6 and about 110 seconds and, by way of example, the second cycle time being between about 6 and about 110 seconds. The most critical variable is the duration of the inflow phase. The inflow phase is kept within strictly regulated range by using three seminal elements of the invention; each of these elements alone can independently cause the interruption of the Inflow phase.

The first shut-off mechanism is the "Trigger Pressure" which is a variable target that depends on the compliance of the body cavity. The second back-up mechanism is the "Maximum Pressure" which has two important aspects, namely, safety and the limitation on the duration of inflow phases. The third mechanism to interrupt the Inflow phase is the pre-set Time cap called "Maximum Time".

Still another important aspect of the invention is the "Number of Cycles" delivered in each session. As previously stated, the repetitious nature of the delivery of fluid into and out of the body cavity is seminal to this invention. The "Number of Cycles" of fluid delivery and evacuation must be above a certain critical number to achieve the desired physiologic transformation necessary to reach therapeutic end-points and can range between about 3 and about 100 cycles.

Yet another important aspect of the invention is the rate of fluid inflation ("Inflation Rate"). The range of inflation must be low enough to be tolerated by the body cavity, and high enough to be effective in expanding the cavity. Higher levels of inflation rate can cause pain and spasm, and might not be tolerated by the patient. If the inflation rate is too low it may not cause expansion of the cavity and/or may not deliver sufficient amount of fluid in the limited inflation time allocated within each cycle. In practice, the inflation rate can vary between about 5 milliliters (ml)/second and about 50 ml/second and, by way of example, can optimally be between about 10 ml/second and about 40 ml/second Another important aspect of the invention is the duration of the entire treatment session ("duration of a full treatment"). The duration of a treatment is the sum of durations of every cycle within the treatment. In this regard, it is important that the treatment last long enough to deliver the necessary mechanical stimulation to cause effective therapeutic end-points, including benefiting conditions such as irritable Bowel Syndrome, chronic constipation, bloating, and many other gastrointestinal conditions. In practice, the duration of full treatment can range from between about 1 and about 60 minutes.

Turning to FIG. 11, this figure comprises a graphical representation of cyclical pressure measurements collected in a clinical setting that involved the pressurization and depressurization of the colon of the patient in accordance with the method of this latest embodiment of the invention. Plotted in the graph of FIG. 11 is reference pressure, trigger pressure and duration of inflow for 39 pressurization-depressurization cycles with each cycle being undertaken at a pre-determined pressure. In the conduct of normal treatments, the body cavity is pressurized and depressurized between 3 and 100 times.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A method for rehabilitative treatment of a body cavity using an apparatus for controllably introducing fluids into the body cavity, said apparatus including a fluid flow conduit interconnected with the body cavity, pressurization means operably associated with the fluid flow conduit for introducing fluid under pressure into the fluid flow conduit and sensor means operably interconnected with the fluid flow conduit for sensing fluid pressure within the fluid flow conduit, said method comprising using the pressurization means and the fluid flow conduit, undertaking a plurality of treatment cycles, including a first treatment cycle, comprising the steps of controllably pressurizing the body cavity at a predetermined inflation rate until a predetermined maximum pressure is reached while controllably expanding the body cavity; using the sensor means to measure the pressure within the body cavity to ascertain when the predetermined maximum pressure has been reached; and, upon reaching the predetermined maximum pressure, depressurizing the body cavity for a period of time.

2. The method as defined in claim 1 in which the body cavity is pressurized at an inflation rate of between about 1 milliliter/second and about 50 milliliters/second.

3. The method as defined in claim 1 in which the pressurization time is between about 1 second and about 50 seconds.

4. The method as defined in claim 1 in which the time of the first cycle is between about 6 seconds and about 110 seconds.

5. The method as defined in claim 1 including a further step of, following the pressurizing and depressurizing of the body cavity, using the pressurization means and the fluid flow conduit to undertake a second treatment cycle, comprising the steps of repressurizing the body cavity to a predetermined first pressure of between about 15 mm Hg and about 100 mm Hg to controllably reexpand the body cavity and upon reaching said first pressure, depressurizing the body cavity for a period of time of between about 5 seconds and about 60 seconds.

6. The method as defined in claim 5 in which the time of said second treatment cycle is between about 6 and 110 seconds.

7. The method as defined in claim 6 in which third, fourth, and fifth treatment cycles are undertaken at up to a predetermined pressure.

8. The method as defined in claim 5 in which the body cavity is the colon and in which the method includes the further step of following the pressurization and depressurization of the colon, using the pressurization means and the fluid flow conduit to undertake a third treatment cycle, comprising the steps of repressurizing the body cavity to a calculated second pressure equal to or less than said first pressure to controllably reexpand the colon.

9. The method as defined in claim 8 including a further step following the pressurization and repressurization of the colon, using the pressurization means and the fluid flow conduit to undertake a fourth treatment cycle, comprising the steps of repressurizing the body cavity to a calculated third pressure equal to or less than said first pressure.

10. A method for rehabilitative treatment of a body cavity using an apparatus for controllably introducing fluids into the body cavity, said apparatus including a fluid flow conduit interconnected with the body cavity, pressurization means operably associated with the fluid flow conduit for introducing fluid under pressure into the fluid flow conduit and sensor means operably interconnected with the fluid flow conduit for sensing fluid pressure within the fluid flow conduit, said method comprising using the pressurization means and the fluid flow conduit, undertaking a first treatment cycle, comprising the steps of controllably pressurizing the body cavity at a predetermined inflation rate until a predetermined maximum pressure of between about 5 mm Hg and about 100 mm Hg is reached while controllably expanding the body cavity; using the sensor means to measure the pressure within the body cavity to ascertain when the predetermined maximum pressure has been reached; and, upon reaching the predetermined maximum pressure, depressurizing the body cavity for a period of time of between 5 seconds and about 60 seconds, said method further comprising undertaking a second treatment cycle comprising the steps of:
  (a) controllably pressurizing the body cavity at a predetermined inflation rate for a period of time equal to a reference time;
  (b) measuring the pressure in the body cavity at said reference time to determine a reference pressure;
  (c) averaging said reference pressure and said maximum pressure to determine a trigger pressure; and
  (d) depressurizing the body cavity when said trigger pressure is reached.

11. The method as defined in claim 10 in which said trigger pressure is between about 5 mm Hg to about 100 mm Hg.

12. The method as defined in claim 11 in which the body cavity is pressurized and depressurized between 3 and 100 times.

13. The method as defined in claim 10 further comprising undertaking a third treatment cycle comprising steps of:
  (a) controllably pressurizing the body cavity at a predetermined inflation rate until said reference time is reached;
  (b) recording the pressure at said reference time to determine the reference pressure, and
  (c) averaging said reference pressure and said maximum pressure to determine a second trigger pressure, and
  (d) depressurizing the body cavity when second trigger pressure is reached.

* * * * *